US009694126B2

(12) United States Patent
Hedmann et al.

(10) Patent No.: US 9,694,126 B2
(45) Date of Patent: Jul. 4, 2017

(54) METHOD FOR ADJUSTING A CONTINUOUS DIALYSATE VOLUME FLOW IN A DIALYSIS MACHINE AND DIALYSIS MACHINE

(75) Inventors: Frank Hedmann, Volkach (DE); Erik Griessmann, Schweinfurt (DE); Joachim Wich-Heiter, Kuernach (DE); Sven Sebesta, Schweinfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1136 days.

(21) Appl. No.: 13/484,765

(22) Filed: May 31, 2012

(65) Prior Publication Data
US 2012/0310148 A1 Dec. 6, 2012

Related U.S. Application Data

(60) Provisional application No. 61/492,952, filed on Jun. 3, 2011.

(30) Foreign Application Priority Data

Jun. 3, 2011 (DE) .................. 10 2011 103 325

(51) Int. Cl.
*A61M 1/28* (2006.01)
*A61M 1/16* (2006.01)
(52) U.S. Cl.
CPC ............ *A61M 1/28* (2013.01); *A61M 1/1601* (2014.02); *A61M 2205/3379* (2013.01); *A61M 2206/22* (2013.01)

(58) Field of Classification Search
CPC ........ A61M 1/28; A61M 1/282; A61M 1/284; A61M 1/1601; A61M 2206/22; A61M 2205/3331–2205/3344; A61M 2205/3351; A61M 2205/3355; A61M 2205/3362; A61M 2205/3379; A61M 1/281; A61M 1/285; A61M 1/287; A61M 1/288; A61M 1/14–1/267; A61M 1/30–1/327; A61M 2205/50–2205/52; A61M 2205/82–2205/8212; A61M 2206/00;
(Continued)

(56) References Cited

U.S. PATENT DOCUMENTS 4,190,536 A 2/1980 Grimsrud
4,473,449 A * 9/1984 Michaels ............ A61M 1/1696
205/555

(Continued)

FOREIGN PATENT DOCUMENTS

DE         28 07 274       8/1978
DE   10 2006 028 986      12/2007
(Continued)

*Primary Examiner* — Kami A Bosworth
(74) *Attorney, Agent, or Firm* — Jacobson Holman, PLLC.

(57) ABSTRACT

A method is provided for adjusting a continuous dialysate volume flow in a dialysis machine with at least two discontinuous pumps and a controller for generating a desired volume flow of the dialysate. The energy for driving the pumps is set to be constant with a value determined corresponding to the pump-time volume of the respective pump stroke and the delivered volume. A dialysis machine for carrying out the aforementioned method is also provided.

16 Claims, 15 Drawing Sheets

(58) Field of Classification Search
CPC .......... A61M 2206/10; A61M 2206/20; A61M 2210/1017
See application file for complete search history.

(56) References Cited

U.S. PATENT DOCUMENTS

| | | | | |
|---|---|---|---|---|
| 2003/0199855 A1* | 10/2003 | Rogers | ............... | A61M 5/14276 604/891.1 |
| 2006/0149220 A1* | 7/2006 | Ullestad | ............ | A61M 5/14276 604/891.1 |
| 2006/0184154 A1* | 8/2006 | Moberg | ............ | A61M 5/14566 604/506 |
| 2006/0254578 A1* | 11/2006 | Boehm | ................. | A61M 11/06 128/200.14 |
| 2007/0073393 A1* | 3/2007 | Kung | .................... | A61M 1/101 623/3.13 |
| 2009/0053083 A1* | 2/2009 | Kopperschmidt | ...... | A61M 1/16 417/476 |
| 2009/0069749 A1* | 3/2009 | Miller | ................. | A61M 5/1413 604/151 |
| 2011/0004351 A1 | 1/2011 | Kelly et al. | | |
| 2011/0186517 A1 | 8/2011 | Hedmann et al. | | |

FOREIGN PATENT DOCUMENTS

| | | |
|---|---|---|
| DE | 10 2009 060 330 | 6/2011 |
| DE | 10 2010 031 793 | 2/2012 |

\* cited by examiner

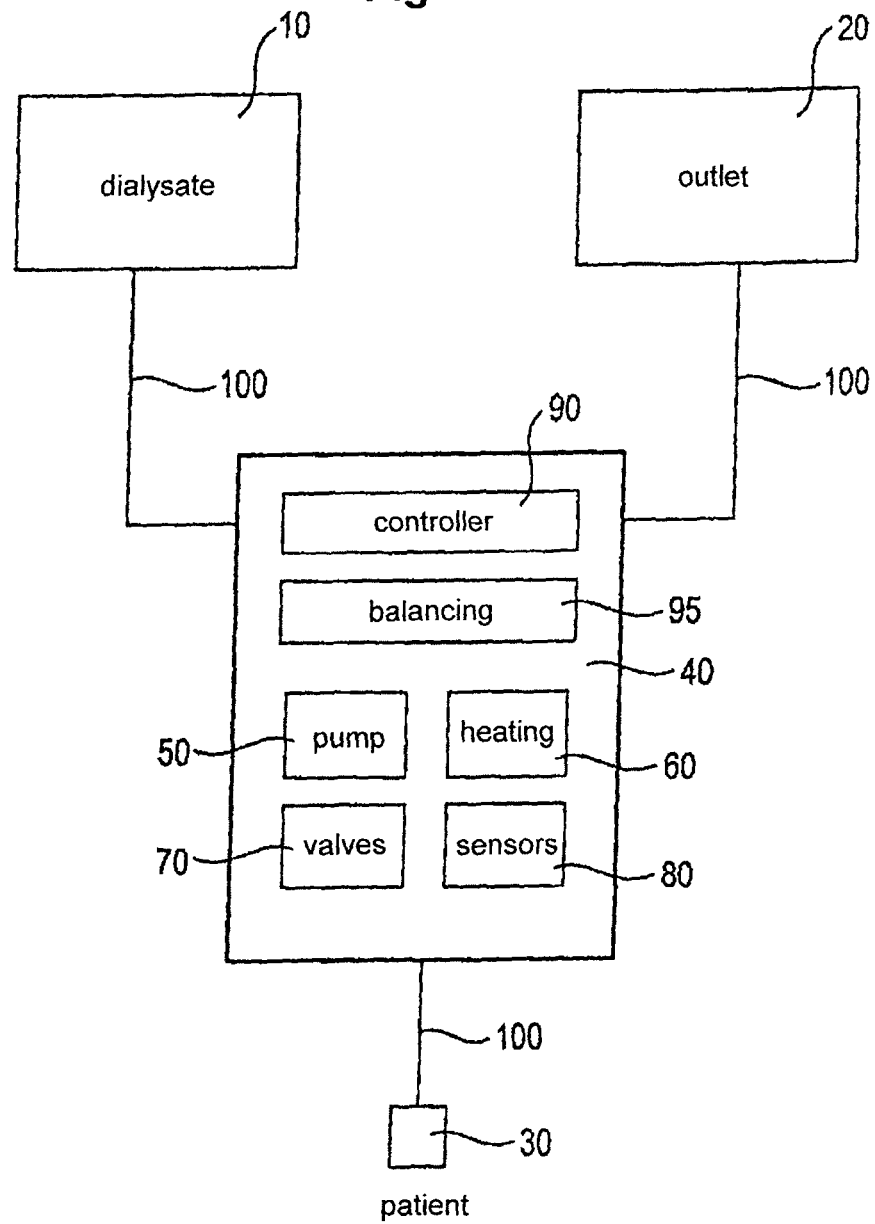

Fig. 17 determining a constant energy for driving a pump in a first pump stroke by taking the constant energy as an estimate from an estimate table.   /250

↓ operating the pump with an amount of energy corresponding to the first constant energy   /260

↓ measuring a pressure in the dialysate delivered and stopping the movement of the pump upon exceedance of a maximum specified system pressure $P_{PatMax}$   /270

↓ determining a constant energy for driving a pump in the pump stroke by taking account of the pump-time volume, the delivered volume and the exceedance of the maximum specified system pressure $P_{PatMax}$.   /280

↓ operating the pump with an amount of energy corresponding to the constant energy   /290

METHOD FOR ADJUSTING A CONTINUOUS DIALYSATE VOLUME FLOW IN A DIALYSIS MACHINE AND DIALYSIS MACHINE

This application claims the benefit of U.S. provisional application No. 61/492,952, filed Jun. 3, 2011, and priority of German number 10 2011 103 325.8 filed Jun. 3, 2011, hereby incorporated by reference.

BACKGROUND OF THE INVENTION

1. Field of the Invention
2. Description of the Related Art

This invention relates to a method for adjusting a continuous dialysate volume flow in a dialysis machine and a dialysis machine for carrying out the method. The dialysis machine in particular can be a peritoneal dialysis machine.

In the automatic peritoneal dialysis a dialysis machine controls and monitors the introduction of the fresh dialysate into the abdominal cavity and the discharge of the used dialysate. Such dialysis machine, also referred to as cycler, usually fills and drains the abdominal cavity several times during the night, i.e. while the patient sleeps.

A peritoneal dialysis machine according to the prior art is shown in FIG. 14 by way of example. As shown here, two pumps 50 usually are employed, which include diaphragm pumps as pump actuators 51. The same act on pump chambers with which dialysate is pumped from correspondingly present dialysate bags into the abdominal cavity of a patient and used dialysate is discharged from the abdominal cavity of the patient. To achieve a constant dialysate volume flow despite the discontinuously operating diaphragm pump, the hydraulic pressure $P_{hyd}$ in the hydraulic lines of the diaphragm pumps is determined. For the case that the diaphragm pumps are driven pneumatically, the corresponding pneumatic pressure in the lines is determined. To ensure pressure monitoring, the pressures $P_{hyd}$ measured by means of the pressure sensors 55 must be compensated by some influence values. These are on the one hand the respective diaphragm pressure $P_{diaphragm}$, i.e. the back pressure which is caused by the deflection and internal tension of the diaphragm in response to the measured hydraulic pressure $P_{hyd}$. With increasing deflection the diaphragm tension increases disproportionately, which is accompanied by a constructionally caused velocity reaction. This back pressure depends on the position L of the hydraulic pump 58, which usually is measured via a displacement transducer 56. In addition, the back pressure $P_{FR}$, which is caused by the flow resistance in the system, i.e. in the pump 50 and in the pump chamber 53 designed as disposable, is taken into account as further compensation variable. This back pressure to be taken into account is dependent on the velocity v in the system.

Finally, the hydrostatic pressure $P_{stat}$ must be taken into account, which results from the position of the patient.

The procedure usually is as follows:

Initially, the diaphragm compensation is measured. The hydraulic pump 58 travels along the entire working path and picks up the existing pressure value in equidistant intervals, which are verified by the displacement transducer 56, and plots the same in a curve. This curve provides for compensating the originally measured raw value of the hydraulic pressure $P_{hyd}$ by the back pressure of the diaphragm $P_{diaphragm}$. The velocity compensation, i.e. the back pressure $P_{FR}$ which is caused by the volume flow resistance, is firmly stored in the method and need therefore not be measured. For the configuration, the same is determined in advance and stored in a corresponding memory.

The detection of the hydrostatic patient pressure $P_{stat}$ is possible at the beginning of each outflow phase. When filling the dialysate or when discharging the dialysate, the system usually will specify a desired volume flow for the phases "Fill/Drain". The objective is to produce a continuous flow. Achieving this objective is rendered more difficult by using two discontinuous pumps.

As shown in the velocity/path diagram of FIG. 15, an individual pump chamber is accelerated at the beginning of the pumping stroke and decelerated at the end of the pumping stroke. During the acceleration phase, i.e. the so-called ramp-up, and the deceleration phase, i.e. the so-called ramp-down, the pumped dialysate volume flow varies. To avoid this, as shown schematically in FIG. 15, the ramp-down of a first pump chamber is superimposed by the ramp-up of the second pump chamber such that a constant dialysate volume flow is obtained.

According to the prior art, the specified volume flow of the dialysate is adjusted at the pump described above by means of the displacement transducer 56. However, this leads to a change in pressure of the entire system, which must be evaluated. When a limit value $P_{PatMax}$ is exceeded, the movement of the pump is stopped. This limit value corresponds to the exceedance of a maximum permitted patient pressure limit. To obtain a continuous volume flow in operation of the two pumps, a ramp-up of the volume flow is performed in the chamber ends, as explained above (cf. FIG. 15). Due to this actuation, the following prerequisites and properties are obtained in the system:

First of all, the diaphragm tension $P_{diaphragm}$ at the beginning must be picked up once as curve over the entire range in dependence on the pump position.

This means that the determination of the patient pressure is characterized by this compensation, which leads to inaccuracies, as the length signal of the length sensor to be taken into account only is comparatively difficult to determine.

Since the velocity is adjusted continuously, the system has the property to increase the energy employed in the controller in response to closures of the patient feed line or in the case of a "drained" patient (towards the end of a cycle). This will inevitably cause the exceedance of the previously indicated limit pressure $R_{PatMax}$.

Finally, the internal tension of the diaphragm is increased very much at the chamber ends and acts against the velocity control, whereby the superposition during start-up or shut-down of the pump systems is rendered more difficult.

What is disadvantageous in the prior art system for adjusting the continuous dialysate volume flow in particular are the high requirements to be satisfied by the control system or the measurement system. Since these requirements frequently are not satisfied to the desired extent, a non-uniform run of the hydraulic pumps can occur.

SUMMARY OF THE INVENTION

Therefore, it is the object of the present invention to provide a method for adjusting a continuous dialysate volume flow, which with simple means, i.e. lower requirements for the control systems and measuring devices, leads to a continuous delivery of the dialysate.

In accordance with the invention, the aforementioned object is solved by a method for adjusting a continuous dialysate volume flow in a dialysis machine with at least two discontinuous pumps and a controller for generating a desired volume flow of the dialysate. According to the method, the energy for driving the pump is adjusted to be constant with a value determined corresponding to the pump-time volume of the respective pump and the delivered volume. In accordance with the present invention, a constant energy is determined here for a pump stroke. This leads to a change in pressure of the volume flow in the entire system, which must be evaluated. Since the pump-time volume and the delivered quantity of dialysate are known, the constant energy for the next pump stroke can be determined, so that the pump is operated with exactly this amount of energy corresponding to this exactly determined constant energy. With this type of actuation the following advantageous properties of the entire system are obtained:

With constant energy setting, the system possesses the property to react to closures of the patient feed line or to a "drained" patient (towards the end of a cycle).

The load is increasing, so that with constant amount of energy the velocity is decreasing.

For determining the energy, for example a constant current flow, a constant voltage or a constant electric power can be adjusted in a simple way.

As used herein, "pump-time volume" refers to the volume of fluid that is pumped by a pump per unit of time as is known by persons of skill in the art as pertains to pumping in the medical field. The term is particularly well known when the heart is taken as a pump, in which case reference is made to "heart-time-volume" or "heart-minute-volume" (HMV), the latter of which refers to the volume of blood pumped by the heart (the pump) for an identified time period, namely one minute.

For example, the pressure in the dialysate delivered is measured advantageously. Upon exceedance of an adjustable pressure limit value the pumps are stopped. With the energy set to be constant, the system therefore can possess the property to react to closures of the patient feed line or to a "drained" patient (towards the end of a cycle) when the energy is set too large. The load is increasing, while the velocity remains almost constant, so that the generated pressure exceeds the specified pressure limit value. In this case, the pump is stopped, so that there is no risk that the patient is exposed to too high a dialysate pressure.

Advantageously, the energy set for supplying the pumps is determined for each further pump stroke in a pump cycle by taking account of the pump-time volume, the delivered volume and possibly the exceedance of the pressure limit value. This results in an adaptation of the system to system changes possible due to the running time.

In accordance with a further advantageous aspect of the invention, the energy set for supplying the pumps for the first pump stroke is taken as estimate from an estimate table. Corresponding empirical values are stored here as starting value for the system.

As far as diaphragm pumps are used as discontinuous pumps, the diaphragm characteristic is taken into account in accordance with a further advantageous aspect of the invention. The diaphragm tension can be determined for the case in which the diaphragm pump no longer pumps at the end of a pumping stroke (so-called ramp-down). Furthermore, the point of the diaphragm tension at which no more diaphragm tension acts advantageously can be determined. These two diaphragm values are sufficient for carrying out the method of the invention. In contrast to the prior art it no longer is necessary to pick up the diaphragm characteristic over the entire pump stroke and store the same in a corresponding memory. The method is further simplified thereby.

The above object is also solved by a dialysis machine for performing the aforementioned method with two discontinuous pumps and a control unit for actuating the pump. The control unit according to the present invention includes means for determining the energy to be employed for a pump cycle of the pumps. Here, the energy can be determined via a current or voltage measurement.

In accordance with an advantageous aspect of the dialysis machine the discontinuous pumps consist of diaphragm pumps. Furthermore, there are preferably provided means for determining the diaphragm pressure of the pump diaphragms.

BRIEF DESCRIPTION OF THE DRAWINGS

Further features, details and advantages of the dialysis machine in which the method according to the invention is employed can be taken from the following detailed explanation of the dialysis machine. In the drawing:

FIG. 2 shows a schematic diagram of a peritoneal dialysis system, FIG. 17 shows a block diagram of the method steps according to the present invention.

DETAILED DESCRIPTION OF THE INVENTION

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In the following, the function of a dialysis machine in which the present invention is used should first be described in general. In the exemplary embodiment, the dialysis machine is a peritoneal dialysis machine. In the same or a similar way, the components described below can, however, also be used for a hemodialysis machine.

The peritoneal dialysis is a variant of artificial hemodialysis in which the abdominal membrane (peritoneum) of the patient well supplied with blood is used as the body's own filter membrane. For this purpose, dialysate is introduced into the abdominal cavity via a catheter. According to the principle of osmosis, urine components of the blood now diffuse through the peritoneum into the dialysate present in the abdominal cavity. After a certain dwell time, the dialysate with the urinary constituents is again discharged from the abdominal cavity.

In the automatic peritoneal dialysis a dialysis machine controls and monitors the introduction of the fresh dialysate into the abdominal cavity and the discharge of the used dialysate. Such dialysis machine, also referred to as cycler, usually fills and drains the abdominal cavity several times during the night, i.e. while the patient sleeps.

Figure 1A:
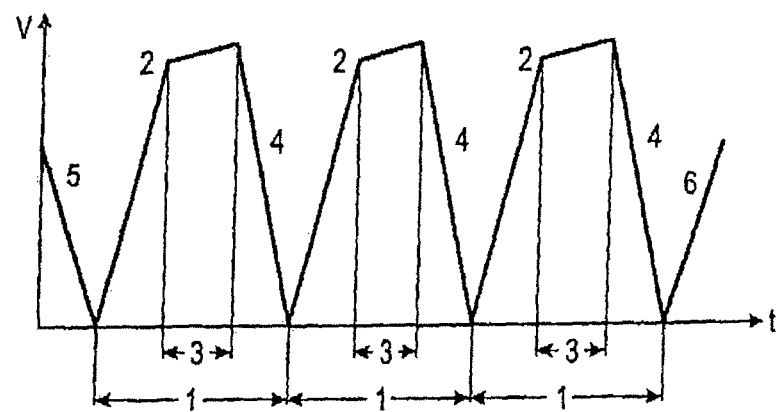
FIGS. 1a, 1b and 1c are three diagrams, respectively, which show typical procedures of an automatic peritoneal dialysis treatment.
Figure 1B:
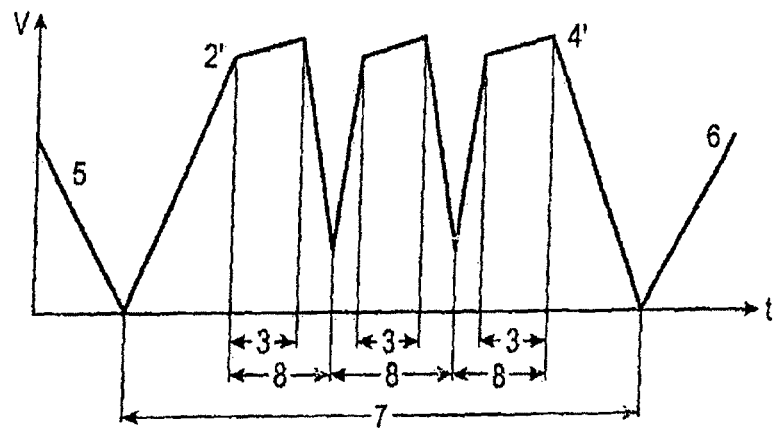
Figure 1C:
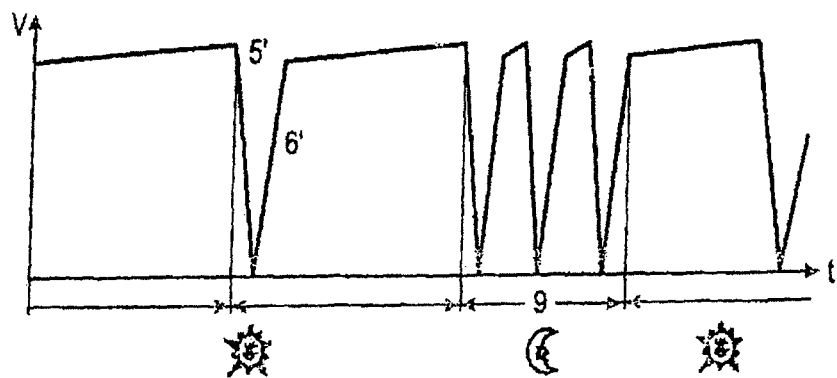

In FIGS. 1a to 1c three different procedures are shown, as they are performed by a dialysis machine. One or more of these procedures usually are stored in the controller of the dialysis machine. Usually, it is possible to adapt the stored procedures to the patient.

In FIGS. 1a to 1c the dialysate volume V present in the abdominal cavity of the patient each is plotted over the time t. FIG. 1a shows the course of a normal automatic peritoneal dialysis treatment over night. At the beginning of the treatment, an initial outflow 5 first is effected, by means of which dialysate is removed, which had been left in the abdominal cavity of the patient during the day. Thereupon, a plurality of treatment cycles 1 are performed, in FIG. 1a three successive treatment cycles 1. Each treatment cycle consists of an inflow phase 2, a dwell phase 3, and an outflow phase 4. During the inflow phase 2, a certain volume of fresh dialysis fluid is introduced into the abdominal cavity of the patient. Depending on the patient, the maximum admissible dialysate quantity is between about 1.5 and 3 l. The fresh dialysate now remains in the abdominal cavity for a certain dwell time 3. Typically, the dwell phase lasts a few hours. Thereupon, the now used dialysate is again discharged from the abdominal cavity in the outflow phase 4. Thereupon, a new treatment cycle starts. The treatment is terminated with a last inflow 6, by means of which a certain quantity of fresh dialysate is introduced into the abdominal cavity of the patient. The same then remains in the abdominal cavity of the patient during the day.

The individual treatment cycles 1, which take place during the night, are actuated automatically by the controller of the dialysis machine. The initial outflow and the last inflow likewise can be actuated automatically by the dialysis machine. Alternatively, the same are activated manually by an operator or by the patient.

In FIG. 1b, a so-called tidal treatment is shown. The same also starts with an initial outflow 5 and ends with a last inflow 6. Furthermore, a base cycle 7 is provided, which is divided into a plurality of tidal cycles 8. There is first provided a base inflow phase 2'. After the dwell phase 3, however, no longer the complete dialysate volume is removed from the abdominal cavity, but only a certain partial quantity of the dialysate present in the abdominal cavity. The same then is replaced by a corresponding volume of fresh dialysate. After another dwell cycle, a further tidal removal can be effected, in which not the entire dialysate present in the abdominal cavity is removed. Towards the end of the base cycle 7 a base outflow phase 4' takes place, in which now the entire dialysate is removed. In FIG. 1b merely one base cycle 1 is shown. Alternatively, however, a plurality of base cycles can also be provided.

FIG. 1c shows the course of a peritoneal dialysis treatment with a so-called PD-Plus treatment. During the night 9, a usual peritoneal dialysis treatment takes place, which can be carried out as shown e.g. in FIG. 1a or 1b. Furthermore, however, an additional PD-Plus treatment is provided during the day, in which the used dialysate is removed in an outflow phase 5' and replaced by fresh dialysate in an inflow phase 6'. In the PD-Plus treatment, a normal nocturnal peritoneal dialysis treatment hence is combined with one or more additional treatment cycles during the day. The procedure of the nocturnal treatment is automatically carried out as usual by the dialysis machine. The treatment cycles during the day likewise are performed and monitored by the machine.

In FIG. 2, the structure of a typical peritoneal dialysis system now is schematically illustrated. The peritoneal dialysis system comprises a container 10 with fresh dialysate and an outlet 20 for used dialysate. Furthermore, a connector 30 is provided, which can be connected to a catheter of the patient, in order to either introduce fresh dialysate into the abdominal cavity of the patient or discharge used dialysate from the abdominal cavity. The container 10 with fresh dialysate, the outlet 20 for used dialysate and the connector 30 to the patient are connected with each other via fluid paths 100 and together with the same form the fluid system of the peritoneal dialysis system.

For carrying out the peritoneal dialysis treatment a dialysis machine 40, also called cycler, is provided. The dialysis machine 40 comprises the following main components:

A pump 50, which is used for the transport of the fluids. The pump 50 delivers the fresh dialysate from the container 10 to the connector 30. Furthermore, the pump 50 can transport the used dialysate from the connector 30 to the outlet 20.

Valves 70, which are used for controlling the fluid flows. The valves 70 open and close the fluid paths 100, in order to create the corresponding fluid connections between the container 10, the connector 30 and the outlet 20.

A heating 60, which brings the fresh dialysate to a temperature of about 37° C., before the same is supplied to the patient. As in the peritoneal dialysis relatively large amounts of dialysate are introduced directly into the abdominal cavity of the patient, the heating 60 is necessary to prevent the patient from undercooling and to avoid an unpleasant feeling due to too cold dialysate.

Sensors 80, via which the proper course of the treatment can be monitored and/or controlled. In particular, temperature sensors can be used. Furthermore, pressure sensors possibly can be used.

All components of the dialysis machine 40 are actuated via a controller 90. The controller 90 in particular actuates the pump 50, the heating 60 and the valves 70 on the basis of the data of the sensors 80. The controller 90 ensures the automatic procedure of the peritoneal dialysis. As an important component, the controller 90 comprises a balancing unit 95, which balances the fluid quantities supplied to and withdrawn from the patient. Balancing prevents that too much fluid is supplied to or too much fluid is withdrawn from the patient.

Balancing 95 can be effected on the basis of the actuation data and/or sensor data for the pump 50 alone. Alternatively, balancing can also be effected via separately provided balancing chambers. It is also possible to use scales for balancing. Such scales weigh for example the weight of the container 10 with fresh dialysate and/or of a container 20 with used dialysate.

As in the peritoneal dialysis the dialysate is administered to the patient directly into the abdominal cavity, utmost sterility must be ensured. Therefore, the fluid paths and the fluid system, which gets in contact with the fresh and/or the used dialysate, usually are designed as disposable part. In particular, the fluid paths and the fluid system are designed as plastic parts. Thus, the same can be supplied in a sterile outer packaging and be unpacked only shortly before the treatment.

Figure 3:
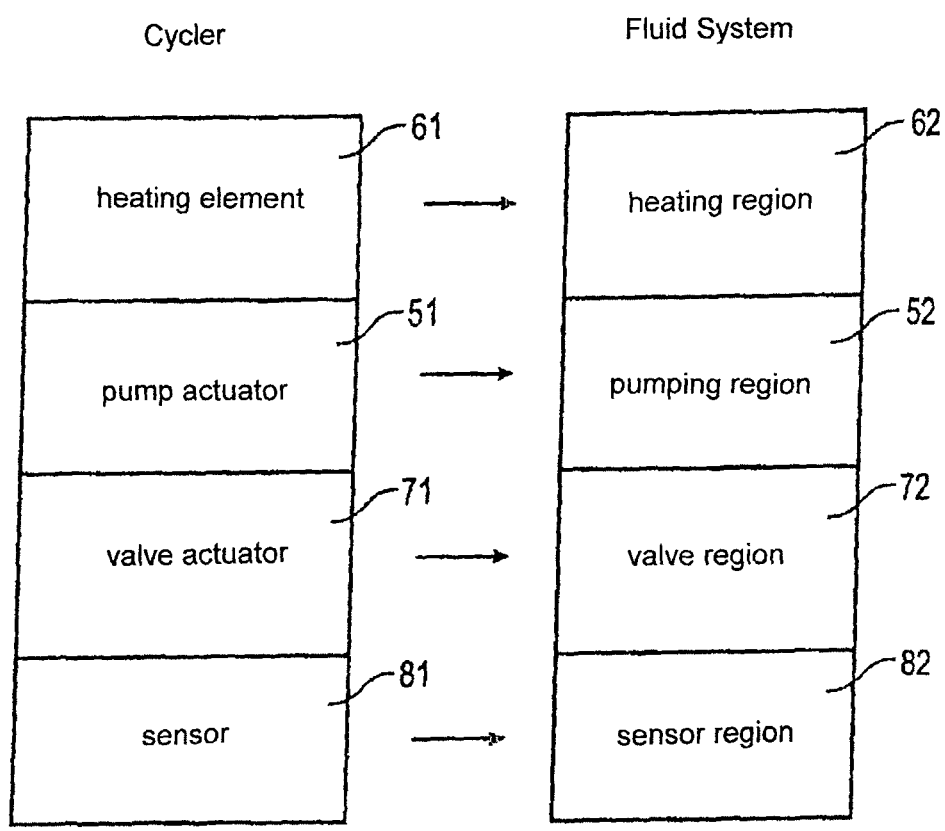
FIG. 3 shows a schematic diagram of the division of the peritoneal dialysis system into a dialysis machine and a fluid system.

To nevertheless provide for a control of the peritoneal dialysis by the dialysis machine 40, the fluid system must be coupled to the dialysis machine 40. FIG. 3 schematically shows how individual elements of the dialysis machine 40 are coupled to corresponding regions of the fluid system.

The dialysis machine 40 includes a heating element 61. The same must be coupled to a corresponding heating region 62 of the fluid system. The coupling provides for the transmission of thermal energy from the heating element 61 to the dialysate present in the heating region 62.

The dialysis machine 40 furthermore includes one or more pump actuators 51 which are coupled with a pumping region 52 of the fluid system. The pump actuators 51 generate a pumping force which is transmitted to the pumping region 52. As a result, the fluid present in the pumping region 52 can be moved along the fluid paths.

Furthermore, the dialysis machine includes one or more valve actuators 71. The same generate a closing movement which is transmitted to corresponding valve regions 72 of the fluid paths. As a result, the valve regions 72 of the fluid paths can be closed and opened correspondingly.

Furthermore, the dialysis machine includes one or more sensors 81. The same are coupled to a corresponding sensor region 82 of the fluid system. As a result, the sensors 81 can measure certain properties of the dialysate. In particular, the temperature of the dialysate thereby can be measured. Furthermore, it can be provided that the pressure in the fluid system is determined.

Of course, the dialysis machine possibly includes further actuators and/or sensors which need not be coupled with the fluid paths.

The individual components of a peritoneal dialysis system will now be explained in detail below with reference to exemplary embodiments.

1. Fluid System
1.1 Dialysate Container

Fresh dialysate usually is provided in plastic bags. Such plastic bags usually have two layers of plastic film, which are welded to each other in an edge region and thus form a container which is filled with fresh dialysate. A hose element usually is welded to this bag, through which the dialysate can be withdrawn from the bag. At the hose element a connector usually is arranged, via which the dialysate container can be connected with the remaining fluid paths. Furthermore, the bag usually includes a recess or eyelet on the side opposite the hose, by means of which the bag can be suspended on a hook. It can thereby be ensured that the dialysate easily flows off from the bag.

The dialysate usually consists of a buffer, an osmotic agent and an electrolyte. As buffer, bicarbonate can be used for example. As osmotic agent, glucose usually is employed. Alternatively, glucose polymers or glucose polymer derivatives can also be employed. The electrolytes usually comprise calcium and sodium.

The dialysate can be heat-sterilized. Advantageously, this is effected after the dialysate has been filled into the bag. In this way, both the dialysate and the bag are heat-sterilized. The filled bag usually is first packed into an outer packaging, whereupon the entire system is sterilized.

As depending on the ingredients the finished dialysate solution often cannot be heat-sterilized or cannot be stored for a long time, it can be provided to separately store individual components of the dialysate and combine them only shortly before the treatment. A first individual solution usually comprises the buffer, whereas a second individual solution comprises glucose and electrolytes. Possibly, more than two individual solutions and hence more than two regions can also be provided in a bag. There can be provided a multi-chamber bag, in particular a dual-chamber bag which includes a plurality of separate regions for storing the individual solutions.

These regions are separated by a connecting element which can be opened mechanically, in order to mix the individual fluids with each other. In particular, a so-called peel seam can be provided between the two regions of the bag, which opens upon application of a certain pressure to at least one of the regions of the bag.

As during a nocturnal peritoneal dialysis treatment relatively large amounts of dialysate are consumed, a plurality of dialysate containers usually are employed in parallel. The same are connected with the fluid paths via corresponding connectors and can be used for filling the patient by correspondingly switching the valves.

1.2 Drainage

To dispose of the used dialysis fluid, the same can either be discharged immediately into the sewage system or first be collected in a drain container. As drain container, a bag usually is likewise employed. Before commencement of the treatment, the same is empty and thus can take up the used dialysate. After termination of the treatment, the bag can then be disposed of correspondingly.

1.3 Cassette

As already described above, the fluid system includes a plurality of regions in which the dialysis machine must act on the fluid system. For this purpose, the fluid system must be coupled to the dialysis machine.

To simplify the coupling of the fluid paths to the dialysis machine and the action of the corresponding elements of the dialysis machine on the fluid paths, cassettes are used. In such a cassette, a plurality of regions in which the dialysis machine acts on the fluid paths are jointly arranged. For this purpose, a cassette usually includes a rigid part made of plastics, in which chambers open towards one side are incorporated as fluid paths. These chambers are covered by a flexible plastic film which provides for coupling to the dialysis machine. The flexible plastic film usually is welded to the rigid part in an edge region. The cassette is pressed to a coupling surface of the dialysis machine, so that the actuators and/or sensors of the dialysis machine get in contact with corresponding regions of the cassette.

The cassette furthermore includes ports for connection of the dialysate container 10, the connector 30 and the outlet 20.

A cassette usually comprises at least one pumping region and one or more valve regions. Via the cassette, the fluid transport through the fluid system can thus be controlled. Furthermore, the cassette can include sensor regions which provide for an easy coupling of sensors of the dialysis machine to the fluid system. Possibly, the cassette furthermore can include one or more heating regions which can be coupled to corresponding heating elements of the dialysis machine.

Figure 4A:
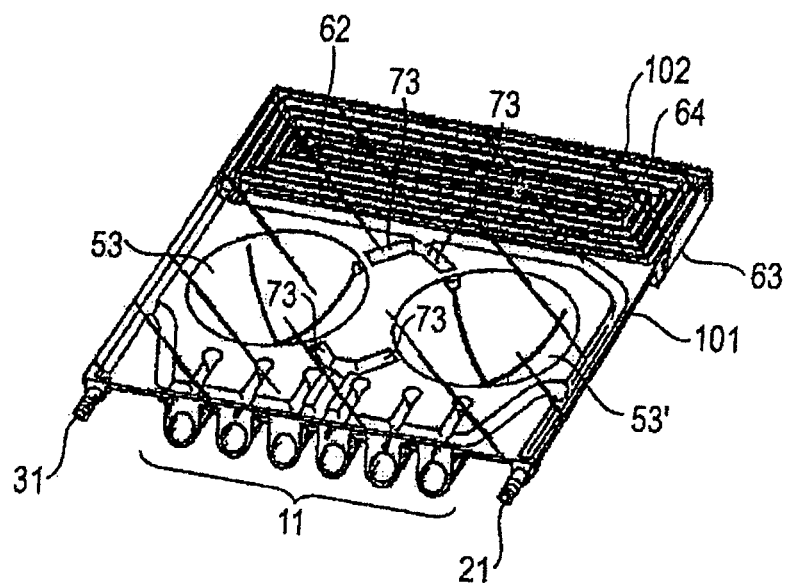
FIGS. 4a and 4b show a first embodiment of a cassette.
Figure 4B:
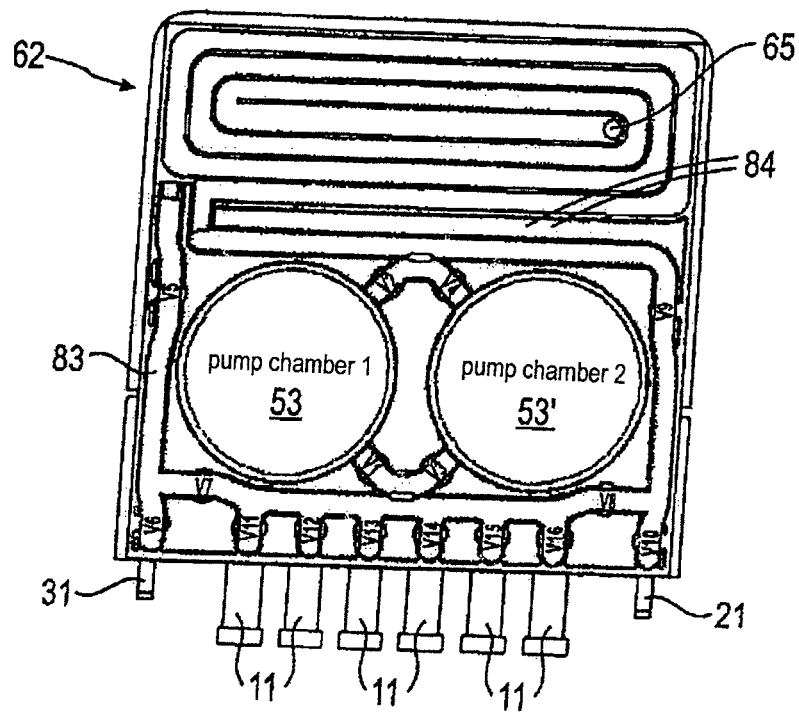

In FIGS. 4a and 4b a first exemplary embodiment of a cassette is shown. The same includes a rigid part 101 made of plastics, in which the fluid paths and coupling regions are incorporated as corresponding recesses, chambers and channels. The rigid part can be fabricated e.g. as an injection-molded part or as a deep-drawn part. The coupling plane of the rigid part 101 is covered by a flexible film 102 which is welded to the rigid part in an edge region. By pressing the cassette to a coupling surface of the dialysis machine, the flexible film 102 is pressed to the rigid part. By pressing the flexible film to the web regions of the rigid part, the fluid paths inside the cassette are separated from each other in a fluid-tight manner.

The cassette includes ports for connection of the cassette to the remaining fluid paths. On the one hand, there is provided a port 21 for connection to the outlet 20 and a connection 21 for connection to the connector 30. At these ports, corresponding hose elements can be provided, which are not shown in FIG. 4a. Furthermore, the cassette includes a plurality of ports 11 for the connection of dialysate containers 10. In the first exemplary embodiment the ports 11 are designed as connectors to which corresponding connector elements can be connected.

The ports each are connected with fluid paths inside the cassette. In these fluid paths valve regions are provided. In these valve regions the flexible film 102 can be pressed into the rigid part 101 via machine-side valve actuators such that the corresponding fluid path is blocked. First of all, the cassette includes a corresponding valve for each port, via which this port can be opened and closed, respectively. To the port 21 for the outlet 20 the valve V10 is associated, to the port 31 for the patient connector 30 the valve V6. To the ports 11 for the dialysate container 10 the valves V11 to V16 are associated.

Furthermore, pump chambers 53 and 53' are provided in the cassette, which can be actuated by corresponding pump actuators of the dialysis machine. The pump chambers 53 and 53' are concave recesses in the rigid part 101, which are covered by the flexible film 102. By means of pump actuators of the dialysis machine the film can now be pressed into the pump chambers 53 and 53' or again be drawn out of these pump chambers. In conjunction with the valves V1 to V4, which switch the inlets and outlets of the pump chambers 53 and 53' and in FIG. 4a have been designated with the reference numeral 73, a pump flow through the cassette can thereby be generated. The pump chambers can be connected with all ports of the cassette via corresponding valve switchings.

Furthermore, a heating region 62 is integrated in the cassette. In this region, the cassette is brought in contact with heating elements of the dialysis machine, which heat the dialysate flowing through this region of the cassette. The heating region 62 includes a channel for the dialysate, which extends spirally over the heating region 62. The channel is formed by webs 64 of the rigid part, which are covered by the flexible film 102.

The heating region 62 is provided on both sides of the cassette. For this purpose, a flexible film also is arranged on the rigid part on the lower surface 63 of the cassette in the heating region. The flexible film likewise is welded to the rigid part in an edge region. On the lower surface, there is also arranged a channel through which the dialysate flows. The channels on the lower surface and on the upper surface are formed by a middle plate of the rigid part, which separates the upper surface from the lower surface and on which webs are provided to the bottom and to the top, which form the channel walls. Initially, the dialysate flows spirally on the upper surface up to the through-hole 65 through the middle plate, from where the dialysate flows back on the lower surface through the corresponding channel. Due to the heating region provided on the upper and the lower surface, the heating surface available for heating up the fluid can be increased correspondingly. However, an embodiment of the cassette in which a heating region only is arranged on one side of the cassette is of course also possible.

Furthermore, embodiments of the cassette are possible, in which a heating element is integrated in the cassette. In particular, an electric heating element such as e.g. a heating coil can be cast into the rigid part of the cassette. As a result, a machine-side heating element can be omitted and the continuous flow heater can be integrated in the cassette. Electric contacts for connecting the electric heating element are arranged on the cassette.

The cassette furthermore includes sensor regions 83 and 84, by means of which temperature sensors of the dialysis machine can be coupled to the cassette. The temperature sensors rest on the flexible film 102 and thus can measure the temperature of the fluid flowing through the channel located thereunder. At the inlet of the heating region two temperature sensors 84 are provided. At the patient-side outlet a temperature sensor 83 is provided, via which the temperature of the dialysate pumped to the patient can be measured.

Figure 5:
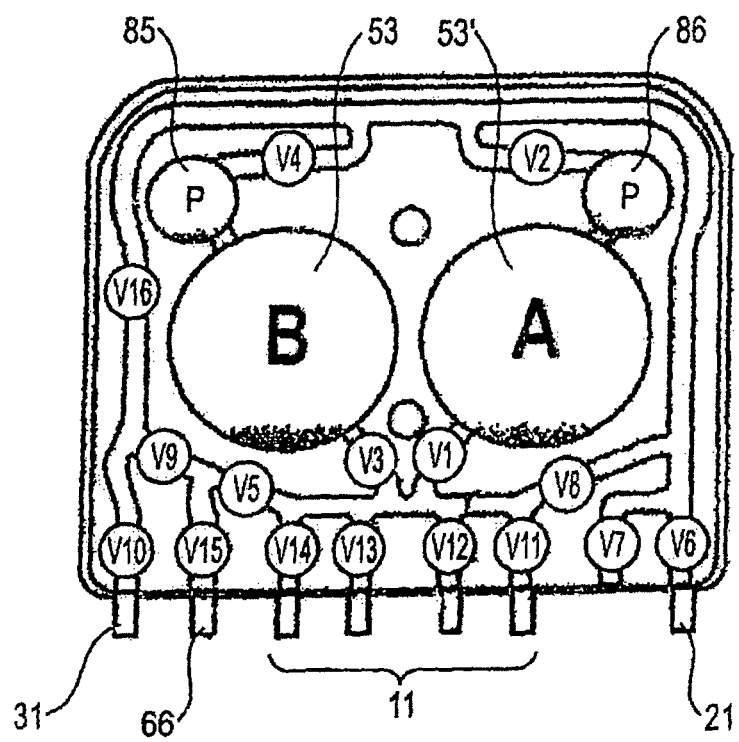
FIG. 5 shows a second embodiment of a cassette.

FIG. 5 shows a second exemplary embodiment of a cassette. In its design, the cassette substantially corresponds to the first exemplary embodiment, but does not comprise a heating region. In use of this cassette, heating therefore is not effected as shown in the first exemplary embodiment via a heating region integrated in the cassette, but e.g. via a heater bag which is placed on a heating plate of the dialysis machine.

The second exemplary embodiment of a cassette as shown in FIG. 5 in turn includes fluid paths which can be opened and closed via valve regions which here likewise are numbered from V1 to V16. Furthermore, the cassette includes ports for connection to further components of the fluid system. Again, there is provided the port 21 for connection to the outlet 20 as well as the port 31 for connection to the connector 30 to the patient. Furthermore, ports 11 are provided for the connection of dialysate containers 10.

In contrast to the first exemplary embodiment, the cassette shown in the second exemplary embodiment includes a further port 66 for connection of a heater bag. For heating the fluid from the dialysate containers 10, the fluid can be pumped into a heater bag via the port 66. This heater bag rests on a heating element, so that the fluid present in the heater bag can be heated. Thereupon, the fluid is pumped from the heater bag to the patient.

In terms of function and design, the pump chambers 53 and 53' and the valves V1 to V4 correspond to the corresponding components in the first exemplary embodiment.

In contrast to the first exemplary embodiment, the cassette of the second exemplary embodiment includes no sensor region for connection of a temperature sensor. The same rather is arranged in the region of the heating elements. The cassette, however, includes measurement regions 85 and 86 for measuring the pressure in the pump chambers 53 and 53'. The measurement regions 85 and 86 are chambers which are in fluid connection with the pump chambers and likewise are covered by the flexible film. To the measurement regions machine-side pressure sensors can be coupled, which measure the pressure in the measurement chambers 85 and 86 and hence in the pump chambers 53 and 53'.

In the second exemplary embodiment the connection of the ports 11, 21, 31 and 66 of the cassette with the further components of the fluid system is effected via hose connections. Connectors possibly are arranged on these hose connections.

1.3 Hoses

The connection between the individual containers of the system, the cassette and the patient connector usually is effected via hose connections. As these are disposable articles, the hoses usually already are firmly connected with a further element at least on one side. For example, hoses can already be provided on one or more of the ports of the cassette. Hoses likewise can already be firmly connected with bags.

1.4 Connections

The fluid system usually is divided in several parts and each sterile packed. For the treatment, these parts must first be connected with each other. In particular, the cassette and the one or more dialysate bags usually are packed separately.

The connection between the individual elements of the fluid system usually is effected via connectors. The connectors are designed such that they provide for a sterile connection between the individual components. This is effected e.g. via corresponding protective films which are opened automatically on closing the connector.

The connection of the individual components can be effected manually by an operator or by the patient himself. Alternatively it can be provided that the connection of the individual components is effected by the dialysis machine.

For this purpose, the corresponding connectors for example can be inserted in a connector receptacle of the dialysis machine and be joined automatically by the dialysis machine.

Furthermore, an electronic controller can be provided, which monitors that the right components of the system are connected with each other. For this purpose, identification means such as bar codes or RFIDs can be provided at the connectors, which identify the components. The dialysis machine comprises an identification means detection unit such as a bar code reader or an RFID detection unit, which detects the identification means on the connectors. In this way, the controller of the peritoneal dialysis can recognize whether the correct connectors have been inserted.

Such examination of the correct composition of the fluid system in particular can be combined with an automatic connection of the connectors. Thus, the system first of all checks whether the right connectors have been inserted in the connector receptacles. The connection between the connectors only is made by the dialysis machine when the right connectors have been inserted. Otherwise, the dialysis machine informs the user that the wrong connectors have been inserted.

2. The Dialysis Machine

The individual components of a dialysis machine will now be described in detail below with reference to two exemplary embodiments.

Figure 6:
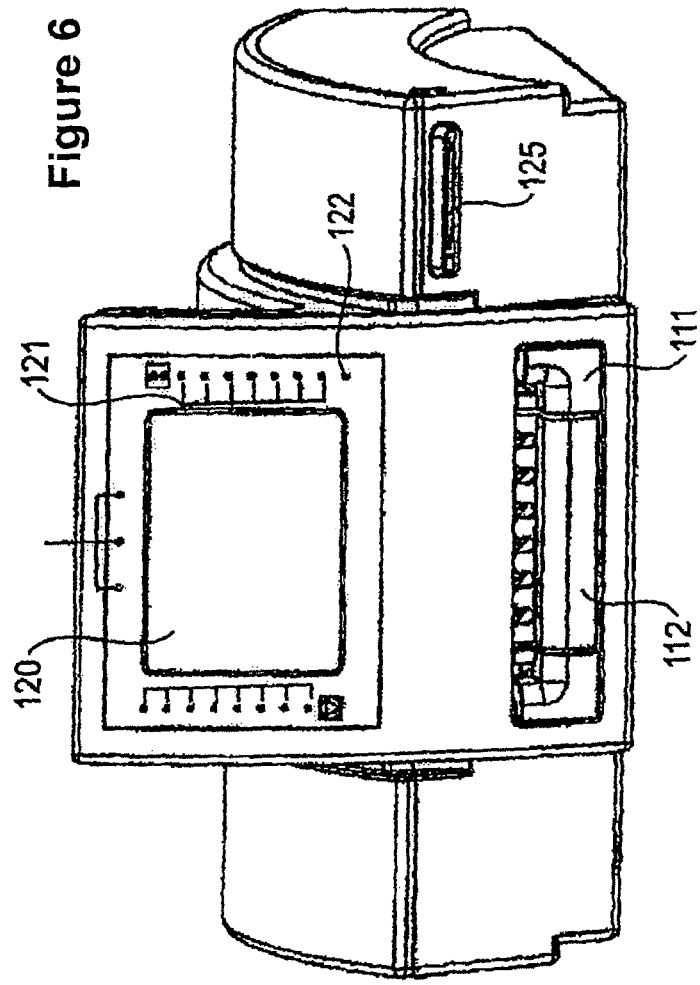
FIG. 6 shows a perspective view of a first embodiment of a dialysis machine.
Figure 7:
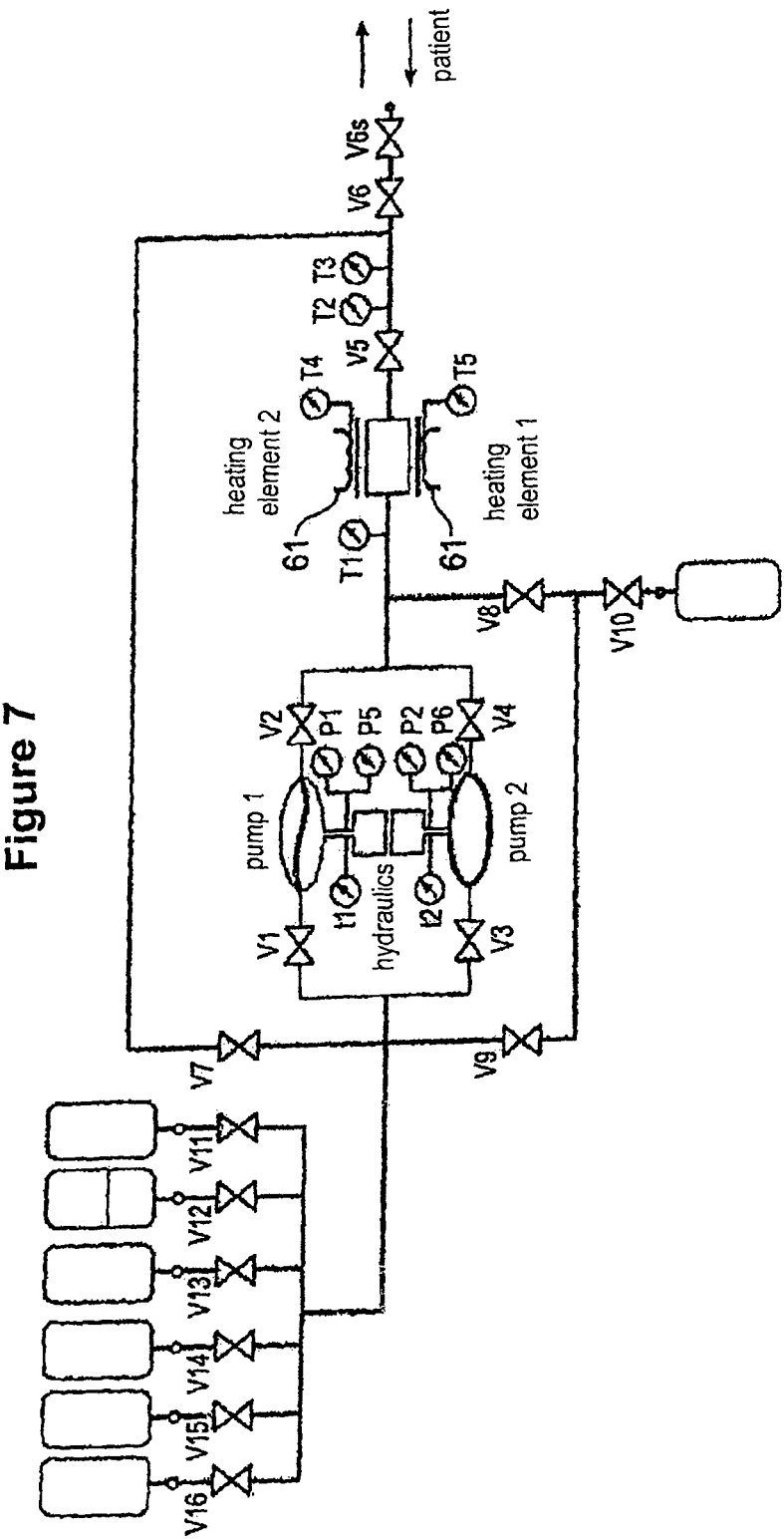
FIG. 7 shows a flow diagram of a first embodiment of a peritoneal dialysis system.

In FIG. 6, a first exemplary embodiment of a dialysis machine is shown, in which the first exemplary embodiment of a cassette is used. The peritoneal dialysis system resulting from the first exemplary embodiment of a dialysis machine and the first exemplary embodiment of a cassette is shown in FIG. 7.

Figure 8:
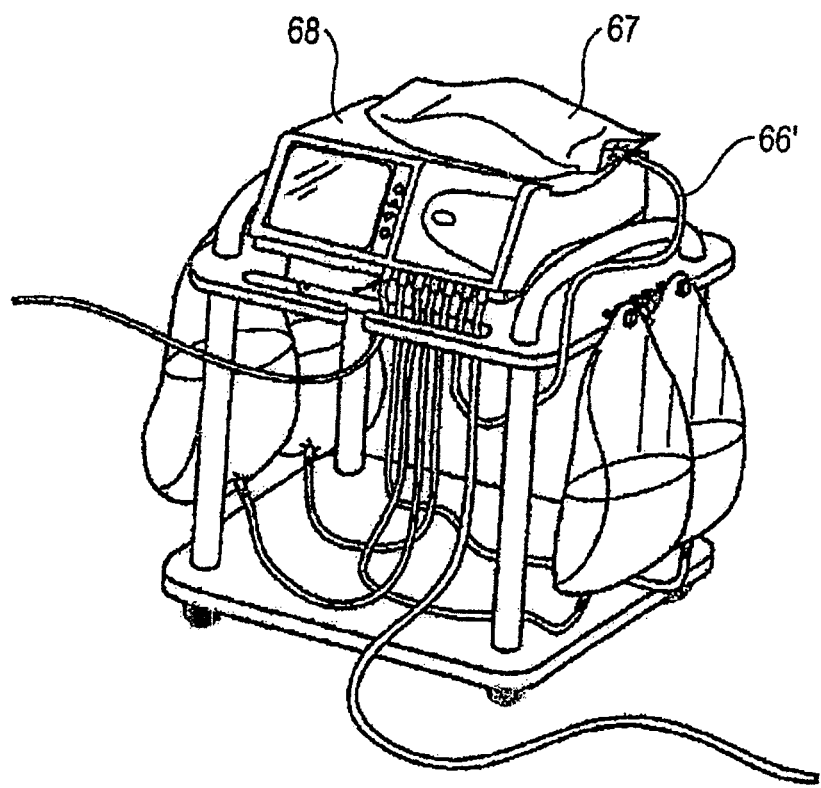
FIG. 8 shows a perspective view of a second embodiment of a dialysis machine.
Figure 9:
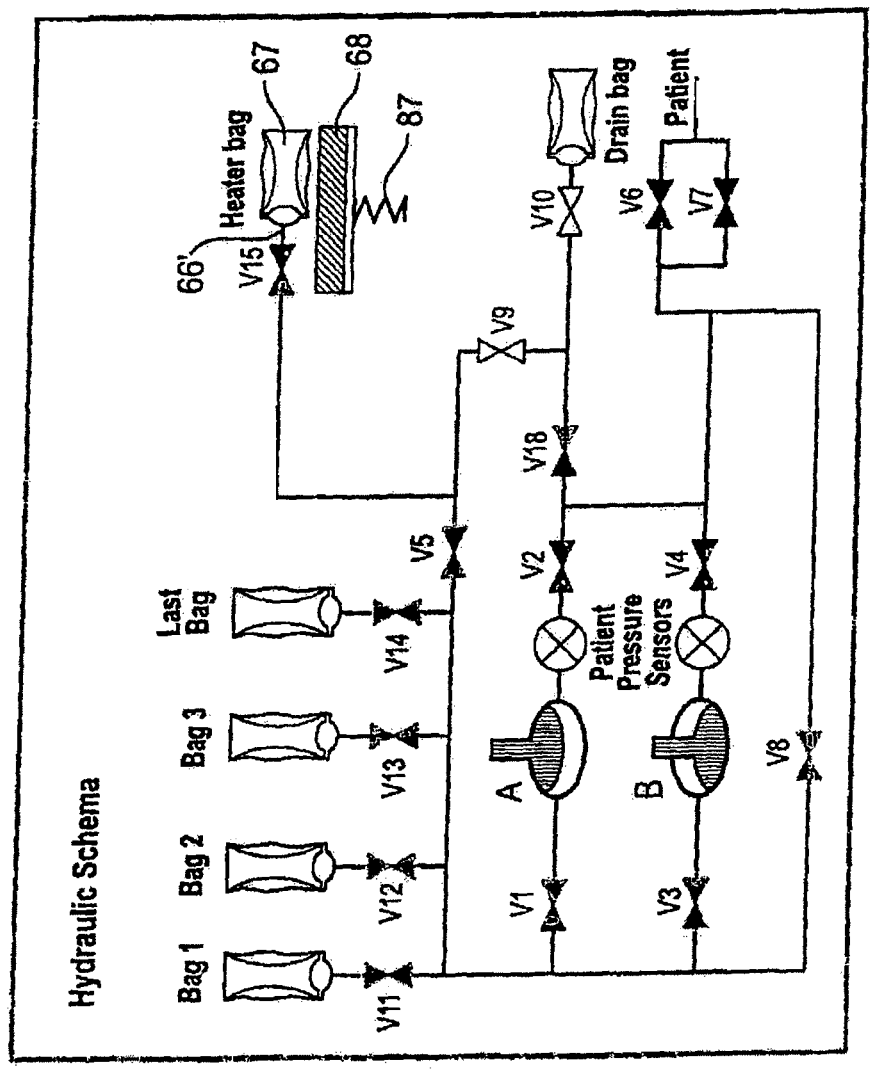
FIG. 9 shows a flow diagram of a second embodiment of a peritoneal dialysis system.

In FIG. 8, a second exemplary embodiment of a dialysis machine is shown, in which the second exemplary embodiment of a cassette is used. The dialysis system resulting from the combination of the second exemplary embodiment of a dialysis machine and the second exemplary embodiment of a cassette then is shown in FIG. 9.

The two exemplary embodiments on the one hand differ in the design of the heating, in the coupling between the dialysis machine and the cassette and in the design of the actuators and sensors.

2.1 Heating

The fresh dialysate must be brought to body temperature, before it is delivered into the abdominal cavity of the patient. For this purpose, the dialysis machine includes a corresponding heating.

Heating usually is effected electrically via one or more heating elements. The heating elements for example can be ceramic heating elements. In such ceramic heating elements a resistance path is applied on a ceramic substrate. By applying a voltage to the resistance path the same is heated, whereby the ceramic substrate material is also heated. The ceramic heating element usually is arranged on a heating plate. The same can be fabricated of aluminum, for example. To the heating plate, the fluid paths in turn are coupled, so that the dialysate present in the fluid paths can be heated.

For heating the fluid, two different configurations are available. On the one hand, a major amount of dialysate can first be heated, which is pumped to the patient only after the heating phase. This is usually effected via a heater bag which rests on a heating plate of the dialysis machine.

The heater bag can be the dialysate bag in which the dialysate is provided. Usually, however, a separate heater bag is employed, into which the dialysate is pumped for heating. When the dialysate in the heater bag has been heated, it is pumped from there to the patient.

Such concept is realized in the second exemplary embodiment of a dialysis machine as shown in FIGS. 8 and 9. There is provided a heater bag 67, which rests on a heating plate 68. The heating plate 68 is arranged on the upper surface of the peritoneal dialysis machine, so that it is easily accessible. The heater bag 67 is connected with the cassette via a line 66'. The cassette includes the valves V5, V9 and V15, via which the heater bag 67 can be connected with the remaining components of the fluid system. Thus, fresh dialysate can be pumped from the dialysate containers 10 via the pump chambers to the heater bag 67. At the beginning of a treatment, the heater bag 67 thus is first filled with cold dialysate. The dialysate in the heater bag 67 then is heated to body temperature via the heating plate 68. Thereupon, the dialysate is pumped to the patient via the pump chambers. Thereupon, the heater bag 67 can be filled again, so that the amount of dialysate required for the next treatment cycle can be heated.

Advantageously, a temperature sensor 88 is provided in the region of the heating plate 68, which is in contact with the heater bag 67 and thus can measure the temperature of the dialysate in the heater bag 67. Furthermore, a temperature sensor can be provided on the heating plate or on the heating element, which measures the temperature of the heating element or the heating plate. A corresponding controller now ensures that the heating plate does not become too hot for the material of the bag.

The heater bag 67 also can take over functions during the balancing of the fluid flows. For example, the heating plate 68 can be part of scales 87, by means of which the weight of the heater bag 67 can be determined. In this way, the fluid quantity which is supplied to the patient after heating can be determined.

As an alternative to the heating of the dialysate via a heater bag as shown in the second exemplary embodiment, the dialysate can also be heated while it is pumped to the patient. The heating thus operates in the form of a flow heater, which heats the dialysate moved through the fluid system, while it is pumped through the fluid paths.

In this concept, a dialysate channel is provided, which is coupled to a heating element of the dialysis machine. While the dialysate flows through the dialysate channel, it absorbs heat from the heating element of the dialysis machine.

Such concept is implemented in the first exemplary embodiment of a dialysis machine, which is shown in FIGS. 6 and 7. The heating region is integrated in the cassette, as has already be explained above. On coupling the cassette to the dialysis machine, the heating region of the cassette thermally gets in contact with heating elements of the dialysis machine.

The heating elements likewise can be designed as ceramic heating elements and be in contact with heating plates which then are coupled to the heating region of the cassette. As already explained with regard to the cassette, a heating plate each is in contact both with the upper surface and with the lower surface of the heating region, which then heats the dialysate flowing through the heating region.

At the inlet and at the outlet of the heating region, temperature sensor regions each are provided in the cassette, which get in contact with temperature sensors of the peritoneal dialysis by coupling to the cassette. By means of the temperature sensors T1 to T3, the temperature of the dialysate flowing into the heating region as well as the temperature of the dialysate flowing out of the heating region can thus be determined. Furthermore, temperature sensors T4 and T5 are provided, which determine the temperature of the heating elements and/or the heating plates.

The use of at least two heating elements provides for interconnecting the heating elements such that with a supply voltage of 220 V they will output substantially the same power as with a supply voltage of 110 V. For this purpose, the two heating elements are operated at 110 V in a parallel connection, whereas with a supply voltage of 220 V they are operated in a serial connection. Such adaptation of the interconnection of the heating elements to the supply voltage can be implemented independent of whether the heating is effected according to the first or the second exemplary embodiment.

2.2 Coupling of the Cassette

To provide for a coupling of the actuators and/or sensors of the dialysis machine to the corresponding regions of the cassette, the dialysis machine includes a cassette receptacle with a coupling surface to which the cassette can be coupled. On the coupling surface the corresponding actuators, sensors and/or heating elements of the dialysis machine are arranged. The cassette is pressed to this coupling surface such that the corresponding actuators, sensors and/or heating elements get in contact with the corresponding regions on the cassette.

Advantageously, a mat of flexible material is provided on the coupling surface of the dialysis machine, in particular a silicone mat. The same ensures that the flexible film of the cassette is pressed to the web regions of the cassette and thus separates the fluid paths inside the cassette from each other.

Advantageously, a circumferential edge of the coupling surface furthermore is provided, which is pressed to the edge region of the cassette. Advantageously, pressing is effected in an air-tight manner, so that a negative pressure can be built up between the coupling surface and the cassette.

Possibly, there can also be provided a vacuum system which can pump off air from the space between coupling surface and cassette. This provides for a particularly good coupling of the actuators, sensors and/or heating elements of the peritoneal dialysis machine with the corresponding regions of the cassette. In addition, the vacuum system provides for a leak test of the cassette. For this purpose, a corresponding vacuum is applied after coupling and it is checked whether this vacuum is maintained.

Pressing the cassette is effected e.g. pneumatically. For this purpose, an air cushion usually is provided, which is filled with compressed air and thus presses the cassette against the coupling surface.

The cassette receptacle usually includes a receiving surface opposite the coupling surface, into which the rigid part of the cassette is inserted. For this purpose, the receiving surface advantageously includes corresponding depressions. The receiving surface with the inserted cassette can then be pressed against the coupling surface by means of a pneumatic pressing device.

Inserting the cassette can be accomplished in different ways. In the first exemplary embodiment of a dialysis machine, which is shown in FIG. 6, a drawer 111 is provided for this purpose, which can be extended from the dialysis machine. Into this drawer the cassette is inserted. The cassette then is pushed into the dialysis machine together with the drawer. Thereupon, the cassette is pressed to the coupling surface, which is arranged in the interior of the machine. Cassette and coupling surface first are moved to each other mechanically and then are pressed together pneumatically.

Figure 10:
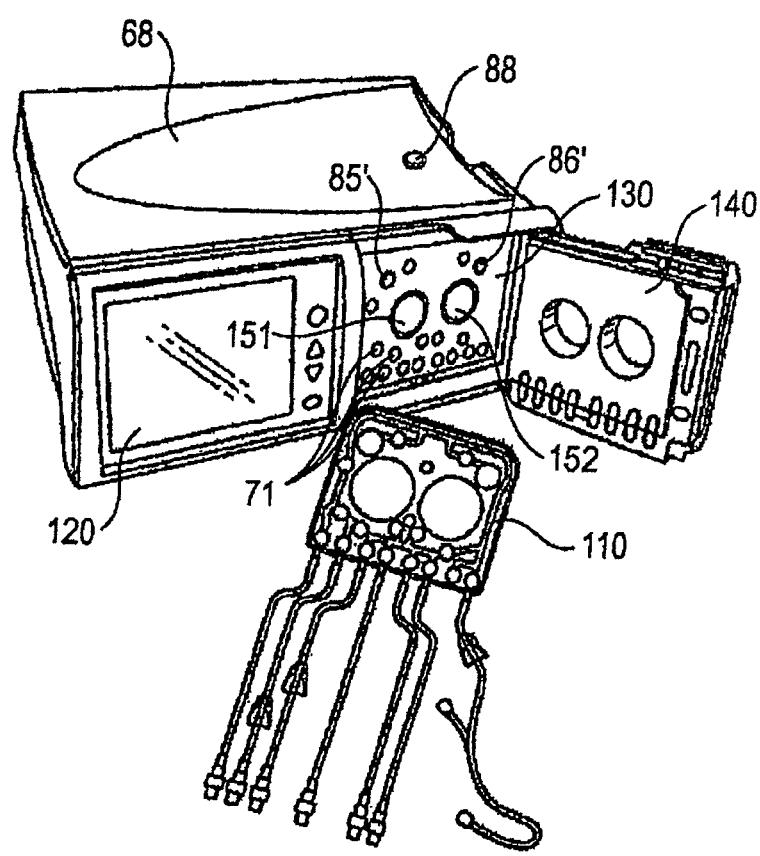
FIG. 10 shows the coupling of the cassette in the second embodiment of a peritoneal dialysis system.

The coupling of a cassette 110 according to the second exemplary embodiment is shown in detail in FIG. 10. The coupling surface 130 is freely accessible by opening a door 140, so that the cassette can be arranged in the right position on the coupling surface 130. The coupling surface 130 is inclined to the rear with respect to the vertical, which provides for easier coupling. Now, the door 140 can be closed, so that a receiving surface on the door gets in contact with the back of the cassette. Pressing now is effected by an air cushion arranged on the door. In addition, a vacuum is applied between the coupling surface and the cassette 110.

The first exemplary embodiment of a dialysis machine furthermore includes a device for connecting automatically. For this purpose, a connector receptacle 112 is provided, into which the connectors of the dialysate bags 10 are inserted. The connector receptacle 112 then moves into the machine, where a bar code reader is provided, which reads the bar codes applied on the connectors. The machine thus can check whether the right bags have been inserted. If the right bags are detected, the connector receptacle 112 moves in completely and thus connects the connectors of the bags to the ports 11 of the cassette designed as connectors.

In the second embodiment, however, such automatic connection has been omitted. Therefore, hose portions are arranged at the ports 11 of the cassette, which must be manually connected with the corresponding bags via connectors.

2.3 Pump Actuators

In the exemplary embodiments, pumping the fluid through the fluid system is effected by a diaphragm pump which is formed by the pump chambers 53 and 53' together with the flexible film of the cassette. When the flexible film is pressed into the pump chamber by a corresponding pump actuator, fluid is pumped from the pump chamber into the open regions of the fluid paths of the cassette. On the other hand, by drawing the film out of the pump chamber fluid is sucked from the fluid paths into the pump chamber.

The pumping stroke is effected by moving a pump actuator into the pump chamber. For the suction stroke, the pump actuator is again moved away from the pump chamber. Due to the air-tight compression of cassette and coupling surface, a negative pressure is obtained, due to which the flexible film of the cassette follows the pump actuator and thus is again drawn out of the pump chamber.

To provide for a good coupling of the pump actuator to the flexible film of the cassette, a vacuum system can also be provided. By adjusting a corresponding vacuum between the coupling surface and the cassette, in particular the force can be adjusted with which the flexible film is maximally moved away from the pump chamber during a suction stroke.

This allows a very fine adjustment of the suction force of the pump. The pumping force, however, is adjusted by the thrust force of the actuator.

The balancing of the fluid flows can be effected by counting the suction and pumping strokes, as the diaphragm pump has a high accuracy of the fluid quantity pumped with each stroke.

2.3.1. Hydraulic Drive

Figure 11:
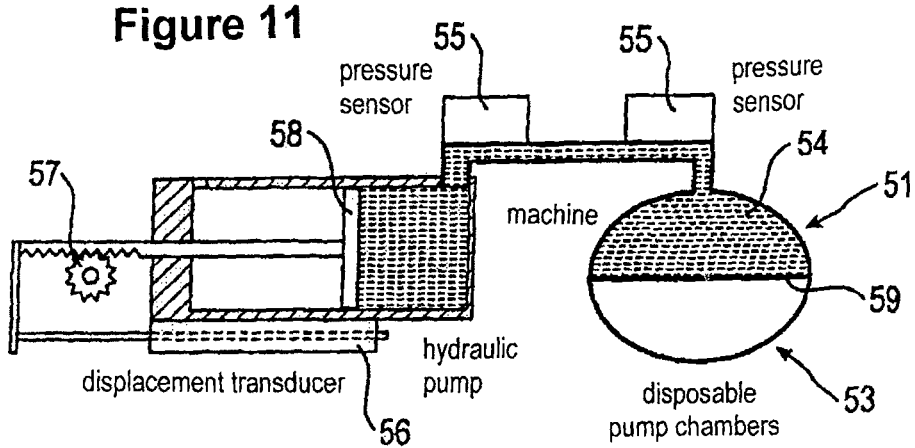
FIG. 11 shows a first embodiment of a pump actuator.

The structure of a first exemplary embodiment of a pump actuator is shown in FIG. 11. The pump actuator is moved hydraulically. For this purpose, a diaphragm 59 is provided, which rests against the flexible film of the cassette. The diaphragm 59 can be made of silicone, for example. Behind the diaphragm 50 a chamber 54 is provided, which can be filled with hydraulic fluid. By applying a positive pressure in the chamber 54, the diaphragm 59 and with the same the flexible film is pressed into the pump chamber 53 of the cassette. By applying a negative pressure to the chamber 54, the diaphragm 59 however is drawn into the chamber 54. Due to the negative pressure between the flexible film and the diaphragm, the flexible film follows this movement, so that the volume of the pump chamber 53 is increased. The pumping operation with the pumping stroke and the suction stroke is schematically illustrated in FIG. 12b.

For operation of the pump hydraulics a hydraulic pump 58 is provided. The same includes a cylinder in which a piston can be reciprocated by means of a motor 57. In this way, the hydraulic fluid is pressed into the chamber 54 via a corresponding connecting line or is again sucked out from this chamber. At the hydraulic pump 58 a displacement transducer 56 is provided, by which the movement of the piston can be picked up. It can thus be determined how much hydraulic fluid has been pressed into the chamber 54 or how much hydraulic fluid has been removed from the same. Furthermore, pressure sensors 55 are provided at the hydraulics, which measure the pressure in the hydraulic system. The same on the one hand provide for a function check of the hydraulics, as the data of the pressure sensors can be compared with those of the displacement transducer 56 and the leak tightness of the hydraulic system can be checked thereby.

In addition, the pressure sensors provide for determining the pressure in the pump chamber 53 of the cassette. When the hydraulic pump 58 is not moved, a pressure equilibrium is obtained between the chamber 54 and the pump chamber 53. The pressure of the hydraulic fluid thus corresponds to the pressure in the pump chamber 53.

Figure 12A:
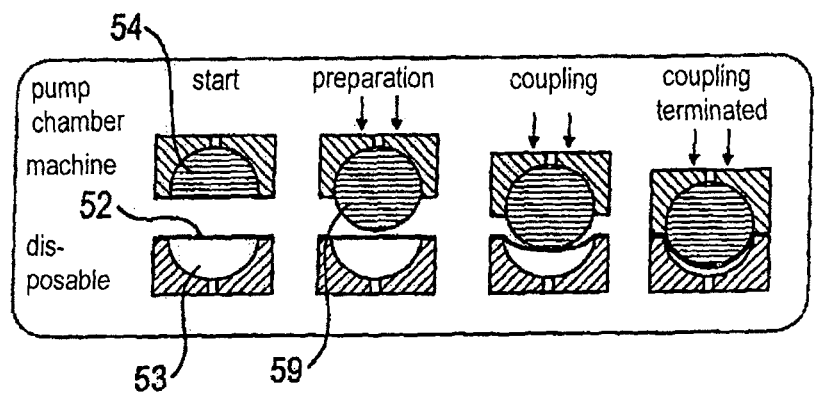
FIGS. 12a and 12b show the coupling of a pumping region of the cassette to a pump actuator.
Figure 12B:
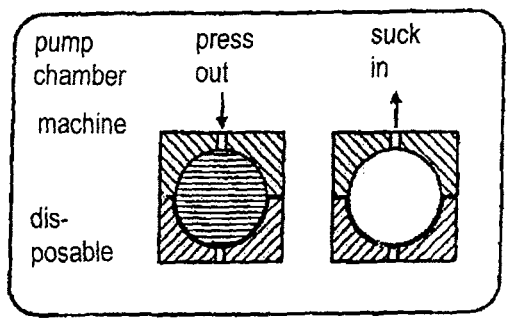

FIG. 12a now shows the operation of coupling the pump actuator to the pump chamber 53. For preparation of the coupling, the chamber 54 first is supplied with hydraulic fluid, so that the membrane 59 bulges to the outside. Thereupon, coupling surface and cassette are moved towards each other, so that the diaphragm 59 presses the flexible film of the cassette into the pump chamber 53. After compressing coupling surface and cassette, the space between the diaphragm and the flexible film is hermetically sealed to the outside, so that the flexible film follows the movement of the diaphragm. This is shown in FIG. 12b.

The pump actuator shown in FIG. 11 is implemented in the first exemplary embodiment of a dialysis machine, as can also be taken from FIG. 7. For each of the two pump chambers 53 and 53' a corresponding pump actuator is provided.

2.3.2 Electromechanical Drive

Alternatively, the pump actuator can also be operated by an electric motor. For this purpose, a correspondingly shaped plunger is provided, which by means of an electric motor, in particular a step motor, is pressed against the flexible film or moved away from the same and thus generates the pumping or suction stroke. Such pump actuators 151 and 152 are shown in the exemplary embodiment of FIG. 10. Advantageously, a vacuum system is provided, which ensures that the flexible film follows the plunger also during the suction movement.

2.3.3 Pneumatic Drive

In accordance with a further alternative, a pump actuator can also be moved pneumatically. There is obtained an operation which largely corresponds to the one as described under item 2.3.1.

2.4 Valve Actuators

As valve actuator a valve tappet can be provided, which presses the flexible film of the cassette into a corresponding chamber of the rigid part and thus closes the fluid channel in this region. The valve actuator can be actuated pneumatically, for example. The tappet can be biased by a spring, so that it either opens pressureless or closes pressureless.

Alternatively, the valve actuator can be implemented by a flexible diaphragm, which is moved hydraulically or pneumatically. The flexible diaphragm is moved by applying pressure against the cassette and thus presses a corresponding valve region of the flexible film into a fluid channel, in order to close the same.

Valve actuators 71, which are coupled to the valve regions V1 to V16 of the cassette, can be seen in FIG. 10 on the coupling surface.

2.5 Sensors

The dialysis machine includes sensors via which the machine can be actuated and the proper operation of the same can be monitored.

On the one hand, one or more temperature sensors are provided, via which the temperature of the dialysate and/or the heating elements can be measured. In the first exemplary embodiment, the temperature sensors are arranged on the coupling surface to the cassette and thus can measure the temperature of the dialysate flowing through the cassette. In the second exemplary embodiment, however, a temperature sensor 88 is provided on the heating plate 68, which measures the temperature of the dialysate present in the bag 67. Furthermore, temperature sensors can be provided on the one or more heating elements.

Furthermore, one or more pressure sensors can be provided, in order to determine the pressure in the pump chambers. It can thus be prevented that dialysate is pressed to the patient with too high pressure or the suction pressure becomes too high when sucking dialysate off from the patient.

In the first exemplary embodiment the pressure measurement is effected via pressure sensors in the hydraulics of the pump actuators, as has been set forth above. In the second exemplary embodiment, however, pressure sensors 85' and 86' are provided in the coupling surface, which directly measure the pressure in corresponding pressure measurement regions of the cassette. The coupling of these pressure sensors to the cassette advantageously is ensured by a vacuum system.

2.6 Input/Output Unit

The dialysis machine furthermore comprises an input/output unit for communication with an operator. For outputting information a corresponding display is provided, which can be implemented for example by light-emitting diodes, LCD displays or a screen. For inputting commands corresponding input elements are provided. There can be provided e.g. push buttons and switches.

In both exemplary embodiments a touchscreen 120 is provided, which provides for an interactive menu navigation. Furthermore, display elements 121 and 122 are provided, which represent conditions of the dialysis machine in a compact manner.

The first exemplary embodiment furthermore includes a card reader 125, via which a patient card can be read in. On the patient card, data for the treatment of the respective patient can be stored. In this way, the course of treatment for the respective patient can be determined individually.

The peritoneal dialysis furthermore includes an acoustic signal unit, via which acoustic signals can be emitted. In particular, an acoustic warning signal can be issued, when an error condition is registered. Advantageously, a loudspeaker is provided, via which the acoustic signals can be generated.

2.7 Controller

The peritoneal dialysis furthermore includes a controller by which all components can be actuated and monitored. The controller ensures the automatic procedure of the treatment.

Figure 13:
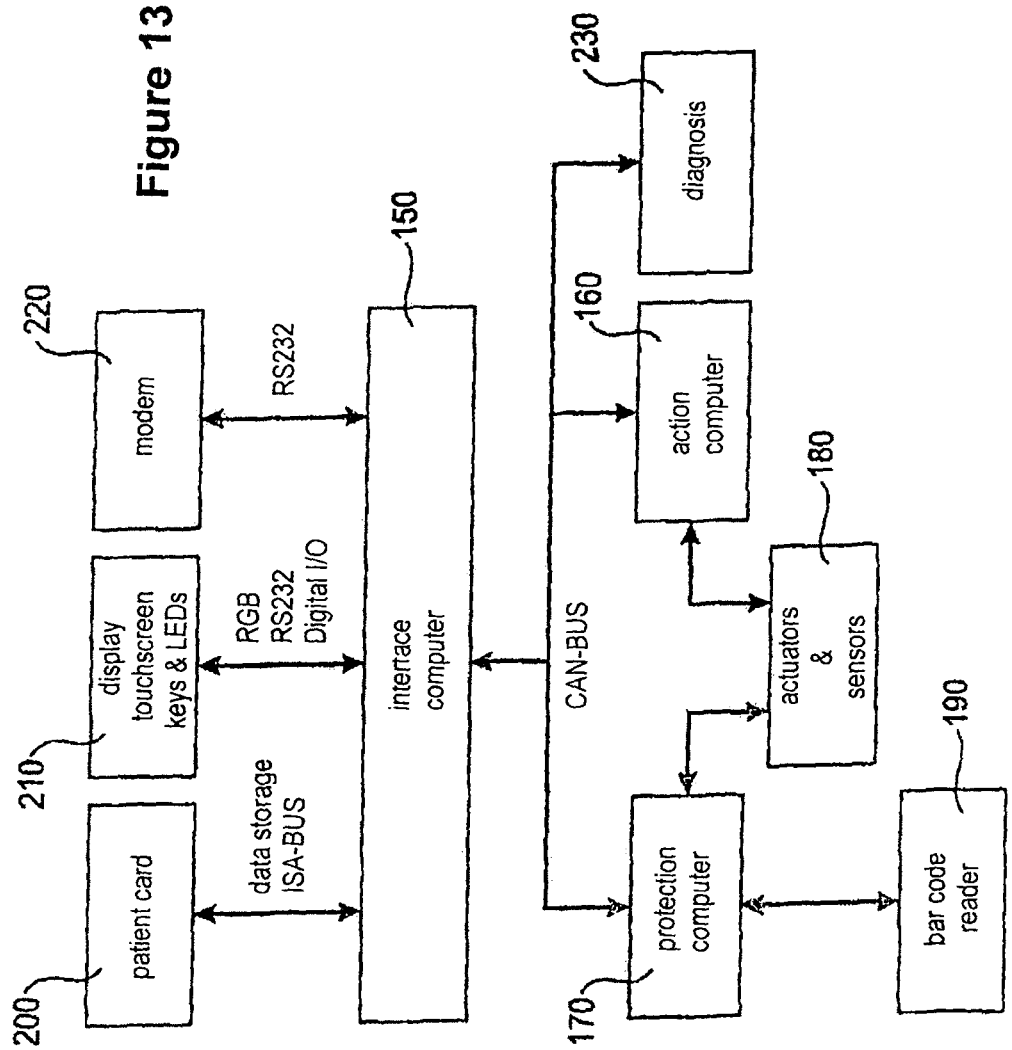
FIG. 13 shows a schematic diagram of the structure of an embodiment of a controller.

In FIG. 13, the basic structure of an exemplary embodiment of such controller is illustrated.

The communication with the operator and with external information sources is effected via an interface computer 150. The same communicates with a patient card reader 200, an input and output unit 210, which serves the communication with the patient, and with a modem 220. Via the modem 220, for example an updated software can be loaded.

Via an internal bus, the interface computer 150 is connected with an action computer 160 and a protection computer 170. The action computer 160 and the protection computer 170 generate a redundancy of the system. The action computer 160 receives signals from the sensors of the system and calculates the control signals for the actuators 180. The protection computer 170 likewise receives signals from the sensors 180 and checks whether the commands issued by the action computer 160 are correct. When the protection computer 170 detects an error, it initiates a corresponding emergency procedure. In particular, the protection computer 170 can trigger an alarm signal. Furthermore, the protection computer 170 can close the access to the patient. For this purpose, a special valve is arranged on the patient-side outlet of the cassette, to which only the protection computer 170 has access. This safety valve is closed in the pressureless condition, so that it will close automatically in the case of a failure of the pneumatics.

The protection computer 170 furthermore is connected with the bar code reader 190 and thus checks the connection of the correct dialysate bags.

Furthermore, a diagnostic system 230 is provided, via which errors of the system can be determined and eliminated.

3. Implementation of the Invention

An exemplary embodiment of the present invention, which is employed in one of the dialysis systems described above or in one of the dialysis machines described above and generally summarized in FIG. 17, will now be explained in the following. The exemplary embodiment of the present invention can be combined with individual or several components as they have been described above.

Figure 14:
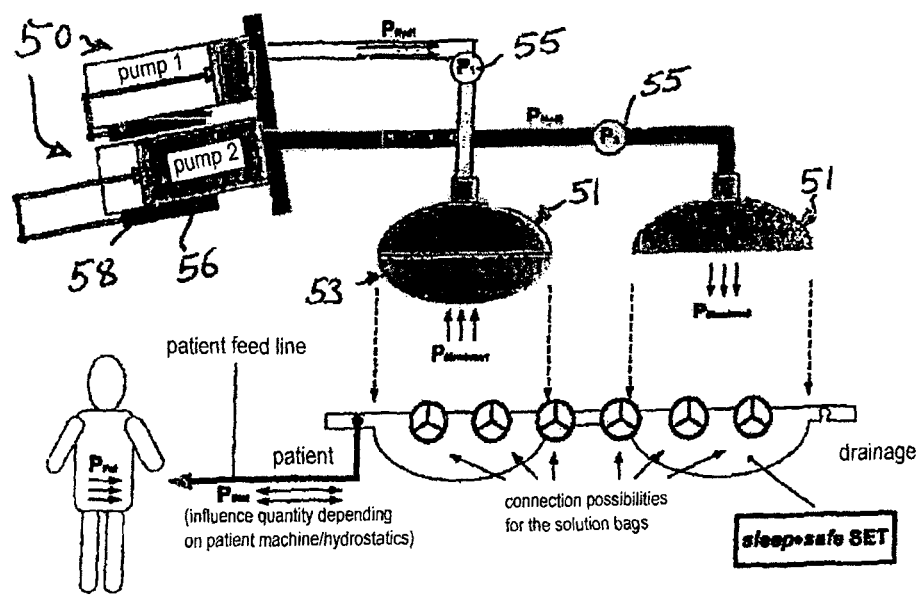
FIG. 14 shows a schematic diagram of the pump system of a peritoneal dialysis system.
Figure 15:
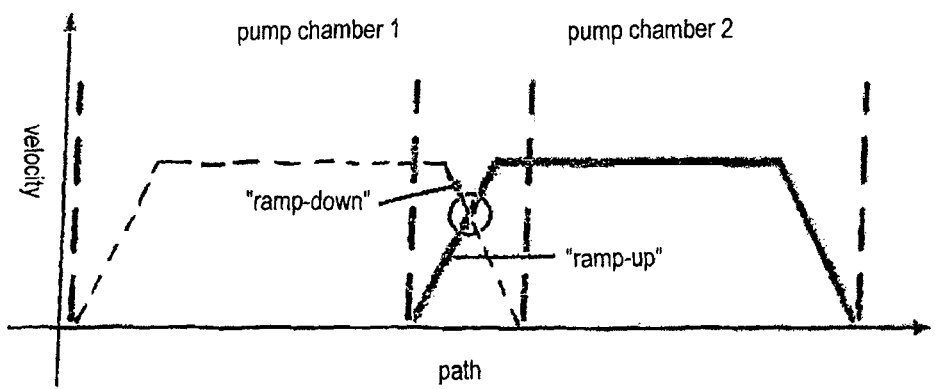
FIG. 15 shows a velocity-path diagram for illustration of the kinematics of the pump chambers.

As explained above, the present invention relates to a method for adjusting a continuous dialysate volume flow in a dialysis machine which in principle is constructed as it has been explained above. The exemplary embodiment described here proceeds from a hydraulic drive of the pump actuators 51, wherein the pump actuators can of course also be driven pneumatically. In accordance with the invention, a continuous volume flow of the dialysate is achieved in that the hydraulic pressure $P_{DesHyd}$ determined by means of the pressure sensor shown in FIG. 14 is determined via a constant energy for a pump stroke, step 250. The actuation of the pump stroke with constant energy, step 260, leads to a volume flow/pressure change in the entire system, which must be evaluated. When a maximum specified system pressure $P_{PatMax}$ is exceeded, step 270, the movement of the pump is stopped. As the pump-time volume and the quantity delivered are known, the constant energy for the next pump stroke can be determined, step 280, and the next pump stroke operated, step 290, with an amount of energy corresponding to the constant energy determined in step 280. Due to this type of actuation, the following properties of the system are obtained:

Since the energy is set to be constant, wherein the energy set corresponds to the ideal setting or is set slightly smaller than ideally required, the system possesses the property to react to closures of the patient feed lines or to already "drained" patients, i.e. patients towards the end of the dialysis cycle, such that the velocity decreases, since the load increases.

However, if the energy is set slightly too large, the system with the energy set to be constant possesses the property to react to closures of the patient feed lines or to a "drained" patient (towards the end of the cycle), in that the load increases, whereas the velocity remains almost constant. As a result, the pressure exceeds the predetermined limit pressure and the pump stops, step 270.

The energy value for the first pump stroke of the cycle is taken from an estimate table, step 250. For each further chamber stroke in this cycle, the energy is adapted by taking account of the pump-time volume, the quantity delivered, and the exceedance of the limit or maximum specified system pressure $P_{PatMax}$, step 280.

Figure 16:
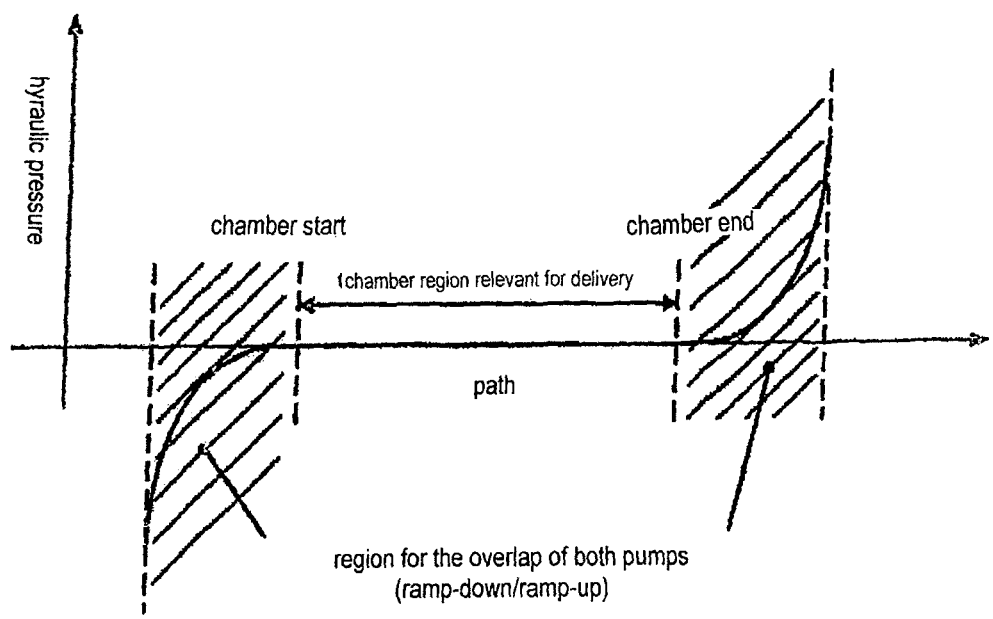
FIG. 16 shows a diagram representing the pressure pattern in a pump chamber.

When using diaphragm pumps, the point of the diaphragm tension $P_{diaphragm}$ must be measured, which designates the so-called ramp-down (i.e. the back pressure to the hydraulic pressure $P_{Hyd}$) of the flow, as can be taken from the diagram in FIG. 16. In this diagram, the hydraulic pressure is plotted over the path. The increase in pressure on ramp-down is represented in the hatched region of the diagram, which is designated with chamber end.

At the same time, the point of the diaphragm tension $P_{diaphragm}$ must be measured, at which no more diaphragm tension $P_{diaphragm}$ acts. In FIG. 16 with the hatched region, this region is designated with chamber start.

The method according to the invention leads to the fact that much smaller demands must be made of the control system or the measurement systems than has been the case so far. This leads to a uniform run of the hydraulic pump 58. At the same time, low volumetric flow rates can be achieved.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A method for adjusting a dialysate volume flow in a dialysis machine with at least one discontinuous pump and a controller for generating a desired volume flow of the dialysate as pumped by said at least one pump over a pump cycle, said pump cycle including a plurality of pump strokes performed sequentially, said method comprising the steps of:
   determining a first constant energy value for a first pump stroke of the at least one pump in said pump cycle;
   operating the at least one pump over the first pump stroke with the first constant energy value;
   determining a constant energy value for each subsequent pump stroke in said pump cycle and operating the at least one pump at the constant energy value determined for said each subsequent pump stroke, the constant energy value for said each subsequent pump stroke being adapted over the pump cycle based on at least one of volume and pressure values measured during at least one previous pump stroke of said plurality of pump strokes.

2. The method according to claim 1, wherein for said first and said each subsequent pump stroke in the pump cycle, a pressure in the dialysate delivered is measured and, upon exceedance of a pressure limit value, the at least one pump is stopped.

3. The method according to claim 2, wherein the determination of the constant energy value for said each subsequent pump stroke depends on whether a pressure limit value was exceeded in at least one previous pump stroke of said plurality of pump strokes.

4. The method according to claim 1, wherein the constant energy value is determined for at least one subsequent pump stroke of said plurality of pump strokes in said pump cycle on the basis of a pump volume per time of the at least one pump and a delivered volume.

5. The method according to claim 1, wherein the constant energy value is determined for at least one subsequent pump stroke of said plurality of pump strokes in said pump cycle on the basis of a pump volume per time of the at least one pump, a delivered volume and whether a pressure limit value was exceeded in at least one previous pump stroke of said plurality of pump strokes.

6. The method according to claim 1, wherein the first constant energy value for the first pump stroke is taken from an estimate table.

7. The method according to claim 1, wherein the at least one pump is a diaphragm pump.

8. The method according to claim 1, wherein the dialysis machine includes, in addition to the at least one discontinuous pump, at least a second discontinuous pump, said discontinuous pumps providing said dialysate volume flow as a continuous dialysate volume flow.

9. The method of claim 1, wherein the steps of operating the at least one pump over the first pump stroke with the first constant energy value and of operating the at least one pump with the constant energy value determined for said each subsequent pump stroke includes at least one form of operation selected from the group consisting of operating the at least one pump with a constant electrical current, operating the at least one pump with a constant electrical voltage and operating the at least on, pump with a constant electrical power.

10. The method of claim 1, wherein said steps of operating the at least one pump over the first pump cycle with the first constant energy vale and of operating the at least one pump with the constant energy value determined for said each subsequent pump stroke include pumping dialysate to a peritoneal cavity of a patient or from a peritoneal cavity of a patient during peritoneal dialysis.

11. A method for adjusting a dialysate volume flow in a dialysis machine with at least one discontinuous pump and a controller for generating a desired volume flow of the dialysate as pumped by said at least one pump over a pump cycle, said pump cycle including a plurality of pump strokes performed sequentially, said method comprising:
   for each pump stroke of said plurality of pump stokes in the pump cycle, performing the following steps:
      determining a constant energy value for the pump stroke;
      operating the at least one pump over the pump stroke with the constant energy value;
      determining whether a pressure during the pump stroke exceeds a pressure limit value; and
   wherein a first constant energy value for a first pump stroke in the pump cycle is taken from a lookup table and, for each subsequent pump stroke in the pump cycle, the constant energy value is adapted depending on whether the pressure limit value was exceeded in a previous pump stroke of said plurality of pump strokes.

12. The method of claim 11, wherein for each pump stroke of said plurality of pump strokes, the at least one pump is stopped if it is determined that the pressure during the pump stroke exceeds the pressure limit value.

13. The method of claim 11, wherein for each pump stroke in the pump cycle, the following additional step is performed:
   determining at least one parameter selected from the group consisting of a pump volume per time of the at least one pump and a delivered volume.

14. The method of claim 13, wherein for said each subsequent pump stroke in the pump cycle, the step of determining the constant energy value includes adapting the constant energy value depending on at least one parameter selected from the group consisting of the pump volume per time of the at least one pump and the delivered volume.

15. The method of claim 11, wherein the step of operating the at least one pump with the constant energy value includes at least one form of operation selected from the group consisting of operating the at least one pump with a constant electrical current, operating the at least one pump with a constant electrical voltage and operating the at least one pump with a constant electrical power.

16. The method of claim 11, wherein said step of operating the at least one pump includes pumping dialysate to a peritoneal cavity of a patient or from a peritoneal cavity of a patient during peritoneal dialysis.

* * * * *